US006274626B1

(12) United States Patent
Jonasse et al.

(10) Patent No.: US 6,274,626 B1
(45) Date of Patent: Aug. 14, 2001

(54) PHENIRAMINE-CONTAINING COMPOSITIONS AND METHOD FOR TREATING ALLERGIC RESPONSES

(75) Inventors: Matthew S. Jonasse, Sodus; Richard V. Smerbeck, Pittsford, both of NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/219,165

(22) Filed: Dec. 22, 1998

(51) Int. Cl.[7] .................................................. A01N 37/10
(52) U.S. Cl. ........................ 514/568; 514/568; 424/78.04
(58) Field of Search ........................... 424/78.04; 514/568

(56) References Cited

U.S. PATENT DOCUMENTS 4,976,969 * 12/1990 Plamondon ........................... 424/672

5,591,426   1/1997  Dabrowski et al. .............. 424/78.04

FOREIGN PATENT DOCUMENTS 0 317 405A1   5/1989  (EP) ................................ A61K/9/06
0 391 002A2  10/1990  (EP) ............................... A61K/31/95

OTHER PUBLICATIONS

Dockhorn R. J. et al. "Comparison of Naphcon–A and its components (naphazoline and pheniramine) in a provocative model of allergic conjunctivitis", Current Eye Research, (1994 May) 13 (5) 319–24, XP000872454 Abstract.

* cited by examiner

*Primary Examiner*—Zohreh Fay

(57) ABSTRACT

This invention relates to compositions comprising pheniramine. In particular, it has been found that pheniramine in combination with n effective amount of a povidone provides improved comfort and reduces the symptoms of dryness compared to compositions with pheniramine alone.

8 Claims, No Drawings

PHENIRAMINE-CONTAINING COMPOSITIONS AND METHOD FOR TREATING ALLERGIC RESPONSES

This invention relates to compositions comprising pheniramine. In particular, it has been found that pheniramine and derivatives thereof, when employed in combination with an effective amount of povidone, provides improved comfort and reduces stinging. Compositions according to the present invention have also been found to alleviate the symptoms of dryness in addition to allergic symptoms.

BACKGROUND OF THE INVENTION

Allergic responses include what is referred to as allergic conjunctiva, which is basically a hypersensitivity reaction, which may occur as a component of hayfever or an independent ocular allergy. For example, allergic responses to ragweed, pollen and animal hair may result in minor eye symptoms of itching and redness. The eye, particularly the conjunctiva, has a relatively large number of mast cells. When allergens are present, they can bind to the immunoglobulin on the surface of these mast cells and trigger the breakdown, or what is known as the degranulation, of the cell. On degranulation, mast cell components, including histamines, are released into the environment outside the mast cell. Through a variety of mechanisms, these components can be responsible for symptoms associated with allergic responses such as itching, redness, lid swelling, vasodilatation and chemosis (edema of the conjunctiva). The patient commonly complains of a burning of the eyes.

Antihistamines are compounds which are administered to prevent histamines, released from mast cells in response to the presence of allergens, from binding to, for example, nerves and smooth muscle cells of the conjunctival blood vessels causing redness, itching and swelling. Thus, topical antihistamines do not block the release of histamine, but rather inhibit the allergic reaction by competing with histamine for the histamine receptors on effector cells. Historically, the term antihistamine has been used to describe drugs that act as $H_1$-receptor antagonists.

Topical antihistamines are commonly formulated in combination with a vasoconstrictor to create a product that also helps to relieve ocular injection. Clinically available antihistamines that competitively antagonize histamine to some extent include ethanolamines, ethylenediamines, alkylamines, phenothiazines or piperidines. Antihistamine preparations commercially available for topical ophthalmic use include 0.3% pheniramine maleate (an alkylamine), 0.5% antazoline phosphate (an ethylenediamine), and 0.1% pyrilamine maleate (also an ethylenediamine). Conventional vasoconstrictors include, for example, ephedrine, naphazoline, phenylephrine, and tetrahydrozoline.

One commercially available product for treating allergic conjunctivitis, OPCON-A® eyedrops, is a sterile aqueous ophthalmic solution containing 0.025% naphazoline hydrochloride and 0.3% pheniramine maleate, further in combination with the inactives hydroxypropyl methylcellulose, sodium chloride, sodium borate, and edetate disodium, preserved with 0.01% benzalkonium chloride. Such products combine the effects of the antihistamine, pheniramine maleate, with the decongestant or vasoconstrictor naphazoline.

In addition to antihistamines used to treat allergic symptoms, a variety of demulcents are known for topical administration to the eye to protect and lubricate mucous membrane surfaces and relieve dryness and irritation. Conventional demulcents include carboxymethyl cellulose, hydroxyethyl cellulose and other cellulose derivatives, dextran, gelatin, and polyols such as glycerin, polyethylene glycol, polysorbate, propylene glycol, polyvinyl alcohol, and povidone. For example, U.S. Pat. No. 4,120,949 discloses the use of polyvinylpryrrolidone (also referred to as povidone or PVP) as a demulcent. Rankin, in U.S. Pat. No. 3,920,810, discloses the use of polyvinylpyrrolidone (PVP) as a demulcent and lubricant in solutions used to treat dry eye. PVP is known to act as a demulcent lubricant by means of a combination of adhesive and lubricating properties that aid in the spreading of its viscous solution.

A problem with products on the market for treating allergic conjunctivitis is that, despite the use of such products, patients continue to complain about burning and itching. Thus, a more effective product or a product treating a greater range of symptoms is desirable. Furthermore, it would be desirable to provide a single composition that would effectively respond to a fuller range of symptoms, including dryness, itching, and burning. It has been found that, contrary to intuition (because allergic responses may include watering of the eyes), dryness is often associated with allergic conditions, and that compositions that alleviate the symptoms of dryness more fully respond to the range of symptoms associated with the allergic responses. It would, therefore, be desirable to be able to effectively and simultaneously treat both dryness and allergic reactions by the administration of a single composition. Finally, it would be desirable if such compositions could be administered to patients irrespective of whether they were wearing contact lenses.

It is, therefore, an object of the present invention to provide improved ophthalmic compositions comprising an antihistamine for treating allergic responses, including redness and itching, that is comfortable and that elicits minimal stinging. It is a further object to provide an ophthalmic composition designed to alleviate dryness. Finally, it is an object to provide methods for treating ophthalmic allergic conditions through administration of the disclosed compositions.

SUMMARY OF THE INVENTION

This invention is directed towards compositions for preventing and treating ophthalmic allergic responses comprising the antihistamine pheniramine or derivatives thereof, in combination with povidone, in the absence or presence of a vasoconstrictor. In accordance with the invention, povidone is employed in the composition not only to improve comfort, but also alleviate dryness. The present compositions have been found to provide effective relief of itchy, red and swollen eyes without producing significant side effects. The compositions can be formulated as solutions or suspensions for topical administration to the eye. In addition, this invention is directed to methods for preventing and treating ophthalmic allergic responses using the compositions of the present invention. The objects, features, and advantages of the various embodiments of the present invention will become more readily apparent from the following detailed description.

DETAILED DESCRIPTION OF THE INVENTION

Pheniramine is a well-established anti-histaminic compound. Pheniramine, the free base and its ophthalmically acceptable salts, is a compound of the alkylamine type that is commonly used as an antihistamine for local and generalized allergic reactions.

In the preferred form of the maleate salt, it is soluble in water and may be represented by the following formula:

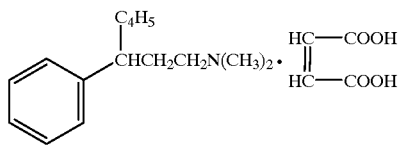

Its chemical name is N, N-dimethyl-gamma-phenyl-2-pyridine-propanamine, butenedoic acid or 1-phenyl-1-(2-pyridyl)-3-dimethylaminopropane maleate. Pheniramine may be prepared in the manner described by Sperber et al. in U.S. Pat. No. 2,567,245 and 2,676,964. Alternately, pheniramine is also commercially available from Loftus Bryan Chemicals Ltd. (Wicklow, Ireland) or Kongo Chemical Co. (Toyama, Japan). Derivatives of pheniramine include, for example, the halogenated derivatives chloropheniramine and bromopheniramine.

According to the present invention, pheniramine (or derivatives thereof), in the amount of 0.10 to 0.50 weight percent, preferably about 0.40 to 0.45 weight percent, in combination with an effective amount of povidone effectively treats the symptoms of both allergy and dryness. The present invention may remove redness, for example, over a period of 5 to 10 minutes. Such compositions have been found to alleviate dryness in combination with the so-called stinging and burning associated with the allergic response.

In addition to pheniramine maleate, other substantially non-toxic or non-irritating pheniramine salts that may be topically administered according to this invention include those derived from organic or inorganic acids such as hydrochloric, hydrobromic, sulfuric, phosphoric. methanesulfonic, acetic, citric, succinic, citric, lactic, tartaric, benzoic acids and the like.

Povidone is a Category I demulcent in the OTC Ophthahnic Drug Products Monograph of the USFDA. Polyvinylpyrrolidone (PVP) is a linear homopolymer or copolymer comprising at least about 80%, preferably at least about 90% of repeat units derived from 1-vinyl-2-pyrrolidone monomers, the polymer more preferably comprising at least about 95% or essentially all of such repeat units, the remainder selected from polymerization-compatible monomers, preferably neutral monomers, such as alkenes or acrylates. Other synonyms for PVP include povidone, polyvidone, 1-vinyl-2-pyrolidinone, and 1-ethenyl-2-pyrolionone (CAS registry number 9003-39-8). PVP has a weight average molecular weight of about 10,000 to 250,000, preferably 30,000 to 100,000. Such materials are sold by various companies, including ISP Technologies, Inc. under the trademark PLASDONE™ K-29/32, BASF under the trademark KOLLIDON™ for USP grade PVP, for example KOLLIDON™ K-30 or K-90 (BASF Corporation, NV Division, 3000 Continental, Mount Olive, N.J. 07628-1234, USA). It is to be understood, however, that the invention is not limited to any specific PVP and that any equivalent PVP of acceptable purity for ophthalmic use, preferably pharmaceutical grade, may be used.

PVP also acts as a water-soluble viscosity builder. Optionally, additional viscosity builders or demulcents may be employed in the present composition, for example, cellulose derivatives, glycerin, and the like. Such viscosity builders or demulcents may be employed in a total amount ranging from about 0.01 to about 5.0 weight percent or less. Suitably, the viscosity of the final formulation is 10 cps to 50 cps.

In the present compositions, povidone is suitably present in a total amount of 0.1 to 5.0% by weight, preferably 0.5 to 2.0 percent by weight of the composition.

The solutions of this invention will also contain water and one or more other components that are commonly present in ophthalmic solutions. In addition to the active ingredients described above, solutions according to the present invention may contain buffers, various surfactants, stabilizers, isotonic agents and the like which aid in making ophthalmic compositions more comfortable to the user. The aqueous solutions of the present invention are typically adjusted with tonicity agents to approximate the osmotic pressure of normal lachrymal fluids which is equivalent to a 0.9% solution of sodium chloride or a 2.5% solution of glycerol. The solutions are made substantially isotonic with physiological saline used alone or in combination, otherwise if simply blended with sterile water and made hypotonic or made hypertonic the lenses will lose their desirable optical parameters. Correspondingly, excess salt or other tonicity agent may result in the formation of a hypertonic solution that will cause stinging and eye irritation. An osmolality of about 225 to 400 mOsm/kg is preferred, more preferably 280 to 320 mOsm/kg.

The pH of the present solutions should be maintained within the range of 5.0 to 8.0, more preferably about 6.0 to 8.0, most preferably about 6.5 to 7.8. Suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred. Generally, buffers will be used in amounts ranging from about 0.05 to 2.5 percent by weight, and preferably, from 0.1 to 1.5 percent.

In addition to buffering agents, in some instances it may be desirable to include sequestering agents in the present solutions in order to bind metal ions that might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent.

As indicated above, the present invention is useful for relieving the symptoms of allergies, including eye irritation, itching and burning, redness, etc. In addition, the compositions are useful for simultaneously treating dryness. Thus, as mentioned above, compositions of the present invention can function as artificial tears and can be used, as needed, for the temporary relief of eye irritation of discomfort. For example, many people suffer from eye conditions in which the eye's tear system fails to provide adequate tear volume or tear film stability necessary to remove irritating environmental contaminants such as dust, pollen, or the like. In persons suffering from the symptoms of dryness, the film on the eye tends to become discontinuous. Because of their emollient and lubricating effect, artificial tears can be used to soothe the eye.

Typically, compositions for treating the symptoms of allergy that have been on the market are not recommended for use with lenses in place. An advantage of one embodiment of the present invention is that the compositions can be used with or without the lenses in place, so that contact lenses do not have to be removed.

The solutions of this invention can be prepared by a variety of techniques, the best mode being illustrated in the Examples below. In general, aqueous ophthalmic solutions used in accordance with this invention may be formulated, for example, in accord with the procedures set forth in Chapter 83 of *Remington's Pharmaceutical Sciences,* 14th Edition, Mack Publishing Company. Such ophthalmic solutions are sterile and may contain a bacteriological preservative to maintain sterility during use. The quaternary ammonium bacteriostats such as benzalkonium chloride are satisfactory for this purpose. An antioxidant may also be employed if desired. By way of example, suitable antioxidants include sodium bisulfite, N-acetylcysteine salts, sodium ascorbate and other water-soluble ophthalmologically acceptable antioxidants known to the pharmaceutical art.

The quantity of a solution according to the present invention to be administered daily, which may vary from 1 to 3 drops, will depend mainly on the severity of the allergy reaction. Compositions according to the present invention can be applied by instilling about 1 or 2 drops in the affected eye(s) as needed, for the temporary relief of symptoms due to allergic reaction.

The following specific experiments and examples demonstrate the compositions and methods of the present invention. However, it is to be understood that these examples are for illustrative purposes only and do not purport to be wholly definitive as to conditions and scope. All percentages are by weight of the solution, unless indicated otherwise.

EXAMPLE I

An example of an aqueous solution of the invention, useful as an ophthalmic solution for the treatment of allergic symptoms is prepared with the following ingredients:

TABLE 1

|  | mg/gm | % w/w |
| --- | --- | --- |
| pheniramine maleate | 4.5 | 0.45 |
| polyvinylpyrrolidone K30 | 20.0 | 2.0 |
| sodium chloride | 3.5 | 0.35 |
| potassium chloride | 3.0 | 0.30 |
| sodium borate | 4.5 | 0.45 |
| sorbic acid | 1.0 | 0.10 |
| boric acid* | 0.0 | 0.00* |
| EDTA | 0.5 | 0.05 |
| q.s. to 100% with purified water | 1.0 | 100 |

*boric acid may be used to adjust pH

The chemical ingredients in Table I are weighed, charged into a 100 Kg vessel with 94.0 kg of purified water, and heated to a temperature >80° C. While initiating agitation, the water temperature is maintained at >80° C. With continued agitation, the following raw materials are added to the batch in the order listed, allowing each to dissolve before adding the next: sodium borate, sorbic acid, EDTA, boric acid, sodium chloride, potassium chloride, pheniramine maleate, and polyvinylpyrrolidone K30. While cooling the batch to 20°–30°, the ingredients are mixed thoroughly for not less than 20 minutes. The solution temperature is maintained between 20° and 30° C. The pH is adjusted as necessary to 7.0 to 7.4 using suitable increments of the appropriate raw material. The batch is brought to its final weight with purified water. The final osmolality is 280 to 330 mOsm/Kg. For packaging, the bottles and caps to be employed are ethylene oxide sterilized and the dropper tips gamma sterilized. The solution is then aseptically dispensed into sterilized bottles by filter sterilization, after which the bottles and caps are aseptically fit into bottles.

EXAMPLE 2

This example illustrates the comfort assessment of four vehicles for use with pheniramine maleate, the latter at a concentration of 0.45%. The comfort of each vehicle in mild to moderate dry eye subjects was evaluated during exposure in a dry-eye chamber. The four formulations tested were as follows;

| Formulation A (Control) | |
| --- | --- |
| 0.35% | Sodium Chloride |
| 0.30% | Potassium Chloride |
| 0.05% | Sodium Borate |
| 0.7% | Boric Acid |
| 1 ppm | PAPB (polyaminopropyl biguanide) |
| Formulation B | |
| 1.0% | Propylene Glycol |
| 0.10% | Sodium Chloride |
| 0.15% | Potassium Chloride |
| 0.07% | Sodium borate |
| 0.70% | Boric Acid |
| 1 ppm | PAPB |
| Formulation C | |
| 2.0% | Polyvinylpyrrolidone K30 |
| 0.30% | Sodium Chloride |
| 0.30% | Potassium Chloride |
| 0.075% | Sodium Borate |
| 0.70% | Boric Acid |
| 1 ppm | PAPB |
| Formulation D | |
| 1.0% | Propylene Glycol |
| 2.0% | Polyvinylpyrrolidone K30 |
| 0.05% | Sodium Chloride |
| 0.15% | Potassium Chloride |
| 0.09% | Sodium Borate |
| 0.70% | Boric Acid |
| 1 ppm | PAPB |

Preliminarily, the medical, medication, and ophthalmic history of the patients were recorded, and an ophthalmic examination, including visual acuity, slit lamp biomicroscopy, fluorescein staining, tear break-up time (TBUT), and Rose Bengal staining was completed. Qualified subjects were randomized to a subject number and then entered the dry eye chamber. At the first visit (visit 1), each patient received one drop of the test solution, which was instilled into the right eye. After 30 minutes and after 60 minutes of exposure, subjects completed a Dry-Eye Comfort Scale Evaluation with respect to the following sensory attributes: burning, stinging, blurry, gritty, dry, tight, scratchy, and foreign body sensation. After 60 minutes of exposure, subjects exited the dry eye chamber. Subjects received a post-exposure ophthalmic examination, including visual acuity, slit lamp biomicroscopy, fluorescein staining, tear break-up time and Rose Bengal staining. At visits 2–4, each subject completed a Baseline Dry Eye Comfort Scale. An ophthalmic exam was again performed including visual acuity, slit lamp biomicroscopy, fluorescein staining, tear break-up time, and Rose Bengal staining. Subjects then entered the dry eye chamber. One drop of a test formulation labeled for the appropriate visit was instilled into the left eye at visit 2, alternating eyes at each subsequent visit. After 30 and 60 minutes exposure, the subjects completed the Dry Eye Comfort Scale Evaluation. After 60 minutes exposure subjects exited the dry eye chamber and the ophthalmic examination completed.

Comfort scores were analyzed for each sensory attribute and for total score of all attributes. Analysis was done as 30 minute score minus baseline score and 60 minutes minus baseline score. None of the formulations showed statistical significance in symptom scores at 30 minutes for burning, blurry, gritty, and tight symptoms. Formulation B showed statistically significant score difference in the dry parameter with an average symptom score change toward improvement of 1.27 units on a nine unit scale. Formulation C showed statistically significant score difference in the stinging and foreign body sensation parameters with an average symptom score change toward improvement of 1.13 units for stinging and 0.80 units for foreign body sensation on a nine unit scale. Formulation D showed statistically significant score difference in the stinging and scratchy parameters with an average symptom score change toward improvement of 0.93 units for stinging and 0.47 units for scratchy on a nine unit scale. Formulation C showed a statistically significant score difference in total symptom score with an average score to improvement of 4.47 units on a 56 unit scale.

Among the formulations, no significant statistical difference was noted at 60 minutes post exposure for the parameters of blurry, gritty, and scratchy. Formulation B showed a statistically significant score difference in the burning parameter with an average symptom score change toward improvement of 0.80 units on a nine unit scale. Formulation C showed statistically significant score difference in the burning and dry parameters with an average symptom score change toward improvement of 1.60 units for burning and 1.07 units for dry on a nine unit scale. Formulation D showed statistically significant score difference in the stinging and tight parameters with an average symptom score change toward improvement of 1.47 units for stinging and 1.07 units for tight on a nine unit scale. Formulation C showed a statistically significant score difference in total symptom score with an average score to improvement of 5.20 units on a nine unit scale. Formulation C demonstrated a statistically significant improvement in total ocular comfort scores at both 30 and 60 minutes post chamber exposure with an average improvement of 4.83 units.

With respect to tear break-up time (TBUT), all values are recorded in seconds and analyze back to baseline. Formulation A (the control) showed an improvement in TBUT at 60 minutes with an average improvement of 1.10 seconds, which may be clinically but not statistically significant. Formulation B showed minimal improvement in TBUT, which is most likely not clinically significant. With respect to Rose Bengal staining, the only statistically significant change in scores was seen with Formulation B. The average change in scores was 0.53 units increased staining on a 4 unit scale at 60 minutes post exposure. With respect to fluorescein staining, the only statistically significant changes in scores were seen with Formulation B. The average change in scores was 0.53 units increased staining on a 4 unit scale at 60 minutes post exposure.

In the analysis, a negative number indicates an improvement with respect to a negative (undesired) attribute, for example, burning. Specifically, Formulation A showed no significant improvements in comfort; mean increase in tear break-up time of 1 second (not statistically significant); Formulation B showed improvement in burning at 60 minutes exposure of −0.80 (p=0.041); improvement in dryness at 60 minutes exposure of −1.07 (p=0.052); mean increase in tear break-up time of 0.263 seconds (not statistically significant); and Formulation C showed improvement in burning at 60 minutes exposure of −1.60 (p=0.033); improvement in dryness at 60 minutes exposure of −1.07 (p=0.052); improvement in total comfort scores at 60 minutes exposure of −5.20 (p=0.002); mean decrease in tear break-up time of 0.488 seconds (not statistically significant);

Formulation D showed improvement in stinging at 60 minutes exposure; improvement in tightness at 60 minutes exposure; mean decrease in tear break-up time of 0.015 seconds. Formulations B, C, and D all show statistically significant improvements in some parameter of comfort after exposure to the dry eye chamber. Formulation C performed substantially the best, exhibiting a one-unit change or improvement in dryness, as well as an overall improvement in total comfort scores of greater than 5 units. In view of the need to provide comfort when using a higher concentration of pheniramine, in addition to the desirability of providing further relief from symptoms such as dryness, the above results indicate that the combination is polyvinylpyrrolidone and pheniramine is unexpectedly superior. Without wishing to be bound by theory, it is surmised that a complexation between povidone and the pheniramine results in the povidone masking any stinging or other adverse side affects due to the pheniramine.

While the invention has been described in conjunction with specific examples thereof, this is illustrative only. Accordingly, many alternatives, modifications, and variations will be apparent to those skilled in the art in light of the foregoing description and it is, therefore, intended to embrace all such alternatives, modifications, and variations as to fall within the spirit and scope of the appended claims.

We claim:

1. A method of treating allergic symptoms and dryness which comprises administering a therapeutically effective amount of an ophthalmic solution comprising (a) from about 0.10 to 0.55 weight percent of pheniramine maleate, a molar equivalent of another salt, or a derivative thereof, and (b) an effective amount of povidone.

2. The method of claim 1, comprising from about 0.40 to 0.50 weight percent of pheniramine maleate or a molar equivalent of another salt thereof.

3. The method of claim 1, wherein the povidone is present in an amount of 0.1 to 5.0 percent by weight of the composition.

4. The method of claim 1, wherein the composition is an aqueous solution and 1 to 3 drops of the solution are instilled in the affected eyes as needed, for the temporary relief of burning and irritation due to allergic reaction.

5. The method of claim 1, wherein the solution is instilled in the eyes while contact lenses are worn.

6. The method of claim 1, wherein the solution is indicated for treating itching, redness, and dryness.

7. A composition useful for relieving or treating itching, redness, dryness or other symptoms associated with allergic symptoms of the eye, comprising:

(a) 0.10 to 0.55 percent by weight of pheniramine maleate, or a molar equivalent of another salt, or a derivative thereof;

(b) 0.5 to 5.0% by weight of povidone;

(c) at least one tonicity agent which is present in an amount of 0.01 to 10.0% by weight;

(d) an effective amount of a buffering agent ; and (e) water.

8. The composition of claim 7, characterized by a pH of 6 to 8 and further comprising a sequestering agent, which is present in an amount of 0.01 to 10% by weight.

\* \* \* \* \*